(12) United States Patent
Kambe et al.

(10) Patent No.: US 6,489,515 B2
(45) Date of Patent: Dec. 3, 2002

(54) GAS-PHASE DEHYDRATION REACTION PROCESS

(75) Inventors: Hideyuki Kambe, Izumiotsu (JP); Shukichi Ugamura, Suita (JP); Yuuji Shimasaki, Otsu (JP); Shinji Takasaki, Settsu (JP)

(73) Assignee: Nippon Shokubai Co., Ltd., Osaka (JP)

( * ) Notice: Subject to any disclaimer, the term of this patent is extended or adjusted under 35 U.S.C. 154(b) by 12 days.

(21) Appl. No.: 09/769,442

(22) Filed: Jan. 26, 2001

(65) Prior Publication Data

US 2001/0014760 A1 Aug. 16, 2001

(30) Foreign Application Priority Data

Jan. 28, 2000 (JP) ........................................ 2000-020349

(51) Int. Cl.⁷ ........................... C07C 41/09; C07C 43/14
(52) U.S. Cl. ..................... 568/687; 548/560; 548/579; 585/654; 585/661
(58) Field of Search ................................ 585/654, 661; 548/560, 579; 568/687

(56) References Cited

U.S. PATENT DOCUMENTS

| | | |
|---|---|---|
| 3,821,245 A | 6/1974 | Kanetaka et al. |
| 4,841,061 A | 6/1989 | Shimasaki et al. |
| 5,304,656 A | 4/1994 | Yano et al. |
| 5,625,076 A | 4/1997 | Shimasaki et al. |
| 5,650,544 A | 7/1997 | Ariyoshi et al. |
| 5,817,886 A | 10/1998 | Ariyoshi et al. |
| 5,847,213 A | 12/1998 | Kurusu et al. |

FOREIGN PATENT DOCUMENTS

| | | |
|---|---|---|
| EP | 9701998 A | 9/1995 |
| EP | 9782985 A | 12/1996 |
| JP | 4740792 | 10/1972 |
| JP | 63126556 | 5/1988 |
| JP | 5202027 | 8/1993 |
| JP | 8141402 | 6/1996 |
| JP | 8143497 | 6/1996 |
| JP | 9235248 | 9/1997 |
| JP | 9241220 | 9/1997 |

Primary Examiner—Shailendra Kumar
(74) Attorney, Agent, or Firm—Sherman & Shalloway

(57) ABSTRACT

Here is provided a process capable of efficiently carrying out a gas-phase dehydration reaction comprising contacting a raw material gas with a solid oxide catalyst containing an alkali metal element to allow reaction to progress by inhibiting decomposition of the raw material and the objective product. This process comprises using a sintered oxide comprising an alkali metal element and silica and/or alumina as a loading material for preheating of the raw material gas and/or as a supporting material for fixation of the position of the catalyst.

32 Claims, No Drawings

GAS-PHASE DEHYDRATION REACTION PROCESS

TECHNICAL FIELD TO WHICH THE INVENTION BELONGS

This invention relates to a gas-phase dehydration reaction process of a hydroxyl group-containing compound. More detailedly, the invention relates to an improvement in a gas-phase dehydration reaction process of a hydroxyl group-containing compound using a solid oxide catalyst containing an alkali metal element.

PRIOR ART

Known as examples of a process of carrying out gas-phase dehydration reaction of a hydroxyl group-containing compound using a solid oxide catalyst containing an alkali metal element are a process of preparing a cyclic amine by gas-phase intermolecular dehydration of an alkanolamine (Japanese Laid-open Patent Publication No. 126556/88, etc.), a process of preparing an unsaturated ether by gas-phase intermolecular dehydration of a glycol ether (Japanese Laid-open Patent Publication No. 143497/96, etc.), a process of preparing an N-alkenylcarboxylic acid amide by gas-phase intermolecular dehydration of a tertiary N-(2-hydroxyalkyl)carboxylic acid amide (Japanese Laid-open Patent Publication No. 141402/96, etc.), a process of preparing an alkylene sulfide by gas-phase intermolecular dehydration of a mercaptoalkanol (Japanese Laid-open Patent Publication No. 202027/93, etc.), a process of preparing a tertiary amine compound by gas-phase intermolecular dehydration of a secondary amine compound and an alcohol (Japanese Laid-open Patent Publication No. 241220/97, etc.), a process of preparing an alkyl ether of a phenol by gas-phase intermolecular dehydration of the phenol and an alcohol (Japanese Laid-open Patent Publication No. 235248/97, etc.).

Hydroxy group-containing compounds as raw materials of the gas-phase dehydration reaction, particularly alkanolamines, glycol ethers and hydroxyethyl compounds such as N-(2-hydroxyalkyl)carboxylic acid amides have a hydroxyl group and an amino group or an amido group or an ether group in the molecule and thermally unstable, and when they contact with an acidic substance at high temperature, decomposition reaction takes place to form acetaldehyde, ethanol and high boiling products. Further, unsaturated ethers, N-alkenylcarboxylic acid amides and cyclic amines as the objective products have a high reactivity and are liable to cause polymerization, formation of high boiling substances, etc. Such reaction would lead not only to a decrease in the reaction yield but also to an increase in the costs for the recovery and purification of the raw materials and the products.

Therefore, in order to put the gas-phase dehydration reaction into an industrial practice, it is important to heat the raw material gas vaporized in the vaporator up to a predetermined temperature without deteriorating it inside the heater (gas preheater) and/or at the inlet side of the catalyst layer in the reactor, and immediately feed it into the catalyst layer, and immediately cool the reaction gas which came out of the catalyst layer.

When the gas-phase dehydration reaction is carried out using a fixed bed reactor, the catalyst needs to be supported by some supporting material for fixing the position of the catalyst. In this occasion, it is important to prevent deterioration of the raw materials and the products on the catalyst supporting material.

However, the above-mentioned official bulletins only describe catalysts capable of converting the raw materials into the objective products selectively at a high space time yield, and they do not describe a process of preheating the raw material gas, a process of cooling the reaction gas and a process of supporting the catalyst at all.

On the other hand, Japanese Patent Publication No. 40792/72 discloses a reaction process comprising gas-phase intermolecular dehydration of N-(2-hydroxyethyl)-2-pyrrolidone to prepare N-vinyl-2-pyrrolidone. This prior art publication discloses loading Raschig rings (outside diameter 5 mm, length 5 mm, porcelain) as an evaporation preheating band of the raw material into the upper part of a vertical stainless steel reaction tube, loading an oxide of zirconium or thorium as a catalyst into a reaction band of the lower part thereof and carrying out gas-phase dehydration reaction. However, it does not disclose decomposition of the raw material at the evaporation preheating band and the composition of the porcelain Raschig ring. Further, Raschig rings for general purposes have problems, for example, that since they have an outside diameter of as large as 4 mm or more and a void ratio of as large as 0.6 to 0.9, they are liable to cause thermal denaturation of the raw material and cannot be used as a supporting material of catalysts having a small particle size.

PROBLEMS TO BE SOLVED BY THE INVENTION

The object of the invention lies in providing, in a gas-phase dehydration reaction process of a hydroxyl group-containing compound using a solid oxide catalyst containing an alkali metal element, the improvement which makes it possible to inhibit decomposition of the raw materials and the objective products thereby to carry out the gas-phase dehydration reaction efficiently.

MEANS FOR SOLVING THE PROBLEMS

The present inventors have intensively studied in order to provide a gas-phase dehydration reaction process capable of solving the above problems, and as a result, they have found that the stability of the raw materials used in the reaction is strikingly influenced not only by the catalyst itself, but by the composition of a loading material for preheating of the raw material gas as well as the composition of a supporting material for fixation of the position of the catalyst.

Thus, the invention provides, a process of gas-phase dehydration reaction comprising contacting a raw material gas with a solid oxide catalyst containing an alkali metal element, wherein a sintered oxide comprising an alkali metal element and silica and/or alumina is used as a loading material for preheating of the raw material gas and/or as a supporting material for fixation of the position of the catalyst.

The invention is particularly useful when the solid oxide catalyst is a solid oxide containing an alkali metal element and silicon.

In the invention, the sintered oxide is preferably a sintered oxide obtained by adding a compound containing an alkali metal element to a sintered oxide comprising an alkali metal element and silica and/or alumina, followed by calcining the mixture.

The invention is useful when the raw material of the gas-phase dehydration reaction is a hydroxyethyl compound represented by the following general formula (I)

$$Z_1\text{—CH}(R_1)\text{—CH}(R_2)\text{—OH} \qquad (I)$$

[wherein $Z_1$ is an amino group, a monoalkylamino group having 1 to 6 carbon atoms, a mercapto group, an alkoxy group having 1 to 10 carbon atoms, an alkylcarboxylic acid amido group wherein the alkylcarboxylic acid moiety has 1 to 6 carbon atoms and the group binding to the N atom of the amido moiety is a hydrogen atom or a methyl group, or a cyclic carboxylic acid amido group including an alkylene group having 3 to 5 carbon atoms and $R_1$ and $R_2$ are each, independently, a hydrogen atom, a methyl group or an ethyl group].

Further, the invention is particularly useful when the gas-phase dehydration reaction is a reaction comprising gas-phase inter-molecular dehydration of a hydroxyethyl compound represented by the following general formula (II)

$$Z_2-CH_2-CH_2-OH \qquad (II)$$

[wherein $Z_2$ is an alkoxy group having 1 to 10 carbon atoms, an alkylcarboxylic acid amido group wherein the alkylcarboxylic acid moiety has 1 to 6 carbon atoms and the group binding to the N atom of the amido moiety is a hydrogen atom or a methyl group, or a cyclic carboxylic acid amido group including an alkylene group having 3 to 5 carbon atoms]
to convert it to a vinyl compound represented by the following general formula (III)

$$Z_2-CH=CH_2 \qquad (III)$$

[wherein $Z_2$ is as defined in the formula (II)].

Further, the invention is particularly useful when the gas-phase dehydration reaction is a reaction comprising gas-phase inter-molecular dehydration of a hydroxyethyl compound represented by the following general formula (IV)

$$R_3-NH-CH_2-CH_2-OH \qquad (IV)$$

[wherein $R_3$ is a hydrogen atom or an alkyl group having 1 to 6 carbon atoms]
to convert it to a cyclic amine represented by the general formula (V)

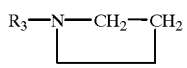
(V)

[wherein $R_3$ is as defined in the formula (IV)].

EMBODIMENTS OF THE INVENTION

The invention is detailedly described below.

The invention is an improvement process applied to a gas-phase dehydration reaction comprising contacting a hydroxyl group-containing compound as a raw material gas with a solid oxide catalyst containing an alkali metal element, preferably a solid oxide catalyst containing an alkali metal element and silicon.

As specific examples of the solid oxide catalyst containing an alkali metal element, when represented by compositions excluding oxygen, there can be mentioned Li—Si, Na—Si, K—Si, Rb—Si, Cs—Si, Na—Al, Na—Zr, Li—Si—P, Na—Si—P, K—Si—P, Rb—Si—P, Cs—Si—P, Na—Mg—Si, Li—Si—Al, Na—K—Si, Na—Cs—Si, Cs—Si—Zr, K—Si—Nb, K—Si—Al—P, Rb—Si—Al—P, Cs—Si—Al—P, Rb—Si—Zr—P, etc., but the invention should not be limited thereto.

As gas-phase dehydration reactions to which the invention is applicable, there can be mentioned various gas-phase dehydration reactions such as a vinylation reaction by intramolecular dehydration of a hydroxyethyl compound, a cyclization reaction by intramolecular dehydration of a hydroxyethylamine, an etherification reaction by intermolecular dehydration between a phenol and an alcohol, and an N-alkylation reaction by intermolecular dehydration between an amine or an amide and an alcohol. However, the invention should not particularly limited to such reactions.

The process of the invention is particularly useful when the raw material of the gas-phase dehydration reaction is a hydroxyethyl compound represented by the following general formula (I)

$$Z_1-CH(R_1)-CH(R_2)-OH \qquad (I)$$

[wherein $Z_1$ is an amino group, a monoalkylamino group having 1 to 6 carbon atoms, a mercapto group, an alkoxy group having 1 to 10 carbon atoms, an alkylcarboxylic acid amido group wherein the alkylcarboxylic acid moiety has 1 to 6 carbon atoms and the group binding to the N atom of the amido moiety is a hydrogen atom or a methyl group, or a cyclic carboxylic acid amido group including an alkylene group having 3 to 5 carbon atoms and $R_1$ and $R_2$ are each, independently, a hydrogen atom, a methyl group or an ethyl group].

As specific examples of the hydroxyethyl compound of the general formula (I), there can be mentioned 2-aminoethanol, 2-(ethylamino) ethanol, N-(2-hydroxyethyl)-2-pyrrolidone, N-(2-hydroxyethyl)-acetamide, N-(2-hydroxyethyl)-formamide, 2-methoxyethanol, 2-ethoxyethanol, 2-isopropoxyethanol, n-propoxyethanol, 2-butoxyethanol, 2-isobutoxyethanol, 2-(2-ethylhexyloxy)ethanol, 2-(2-ethoxyethoxy) ethanol, 2-(2-butoxyethoxy)ethanol, 2-(2-(2-ethoxyethoxy)-ethoxy) ethanol, diethylene glycol, triethylene glycol, etc.

Further, the process of the invention is particularly useful when the gas-phase dehydration reaction is a reaction comprising gas-phase intermolecular dehydration of a hydroxyethyl compound represented by the following general formula (II)

$$Z_2-CH_2-CH_2-OH \qquad (II)$$

[wherein $Z_2$ is an alkoxy group having 1 to 10 carbon atoms, an alkylcarboxylic acid amido group wherein the alkylcarboxylic acid moiety has 1 to 6 carbon atoms and the group binding to the N atom of the amido moiety is a hydrogen atom or a methyl group, or a cyclic carboxylic acid amido group including an alkylene group having 3 to 5 carbon atoms]
to convert it to a vinyl compound represented by the following general formula (III)

$$Z_2-CH=CH_2 \qquad (III)$$

[wherein $Z_2$ is as defined in the formula (II)].

As specific examples of the hydroxyethyl compound of the general formula (II), there can be mentioned N-(2-hydroxyethyl)-2-pyrrolidone, N-(2-hydroxyethyl)-acetamide, N-(2-hydroxyethyl)-formamide, 2-methoxyethanol, 2-ethoxyethanol, 2-isopropoxyethanol, n-propoxyethanol, 2-butoxyethanol, 2-isobutoxyethanol, 2-(2-ethylhexyloxy) ethanol, 2-(2-ethoxyethoxy)ethanol, 2-(2-butoxyethoxy)-ethanol, 2-(2-(2-ethoxyethoxy)ethoxy) ethanol, diethylene glycol, triethylene glycol, etc.

As specific examples of the vinyl compound of the general formula (III), there can be mentioned N-vinyl-2-pyrrolidone, methyl vinyl ether, ethyl vinyl ether, isopropyl vinyl ether, n-propyl vinyl ether, n-butyl vinyl ether, isobutyl vinyl ether, ethylene glycol monovinyl ether, diethylene glycol monovinyl ether, etc.

Further, the process of the invention is particularly useful also when the gas-phase dehydration reaction is a reaction comprising gas-phase intermolecular dehydration of a hydroxyethyl compound represented by the following general formula (IV)

　　(IV)

[wherein $R_3$ is a hydrogen atom or an alkyl group having 1 to 6 carbon atoms]
to convert it to a cyclic amine represented by the general formula (V)

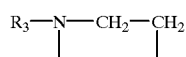　　(V)

[wherein $R_3$ is as defined in the formula (IV)].

As specific examples of the hydroxyethyl compound of the general formula (IV), there can be mentioned 2-aminoethanol, 2-(methylamino)ethanol, 2-(ethylamino) ethanol, etc.

As specific examples of the cyclic amine of the general formula (V), there can be mentioned ethyleneimine, N-methylethyleneimine, N-ethylethyleneimine, etc.

The characteristic of the gas-phase dehydration reaction process of the invention lies in using a sintered oxide comprising an alkali metal element and silica and/or alumina as a loading material for preheating of the raw material gas and/or as a supporting material for fixation of the position of the catalyst in the gas-phase dehydration reaction.

Since the sintered oxide of the invention contains silica and/or alumina and an alkali metal element, the sintering step for obtaining an inert sintered oxide is shortened to realize a reduction in the costs, and moreover, it enables to eliminate unnecessary acid sites which accelerate decomposition of the reaction raw materials. Further, the sintered oxide of the invention is characteristics in that it does not accelerate decomposition of the raw material and the objective product and it does not poison the solid oxide catalyst containing an alkali metal element.

The sintered oxide is a sintered oxide comprising an alkali metal element such as sodium, potassium or cesium and silica and/or alumina.

The sintered oxide may contain an impurity such as an alkaline earth metal (e.g., calcium, magnesium, etc.), iron or titanium. However, since such an impurity may increase unnecessary acid sites or lower the strength of the sintered oxide, the total content of the alkali metal element and silica and/or aluminum metal element in the sintered oxide is made to be usually 80% by weight or more, preferably 95% by weight or more, more preferably 98% by weight or more in terms of its oxide.

The content of the alkali metal element in the sintered oxide is not particularly limited; however, for example, 0.5 to 10% by weight, preferably 2.0 to 8.0% by weight in terms of its oxide. When the content of the alkali metal element is less than 0.5% by weight, the sintering temperature rises, and when it is more than 10% by weight, the loading material becomes strongly basic, which may cause decomposition, condensation, etc. of the raw material and/or the objective product.

The content of silica or alumina in the sintered oxide is not particularly limited; however, for example, 10% by weight or more, preferably 30 to 95% by weight, more preferably 50 to 90% by weight in terms of its oxide.

Above all, a silica-alumina sintered oxide containing 2 to 8% by weight an alkali metal and 10 to 90% by weight silica is preferred. The reason of the preference is that silica-alumina wherein the amounts of the alkali metal element and silica are adjusted to the above range is inactivated at a lower sintering temperature and becomes a sintered oxide having a higher strength, compared with a raw material for a sintered oxide having a higher alumina purity.

Processes for preparing the sintered oxide are not particularly limited, and any processes per se known can be applied. As examples thereof, the following processes can be mentioned.

(1) A process comprising kneading an oxide, hydroxide or carbonate between silicon and/or an aluminum metal element and an alkali metal element together with a binder such as water, an alcohol, an organic acid or a polymer, drying and molding the kneaded matter, and then sintering the molded matter.

(2) A process comprising kneading a clay mineral containing silicon and/or an aluminum metal element such as smectite, montmorillonite, bentonite, kaolin or sericite, and a hydroxide of an alkali metal together with a binder such as water, an alcohol, an organic acid or a polymer, molding and drying the kneaded matter, and then sintering the dried matter.

(3) A process comprising adding commercially available molded alumina, silica-alumina or silica to an aqueous solution of an alkali metal element, making impregnation progress for several hours, drying the resulting matter, and then sintering the dried matter.

The sintering temperature in preparation of the sintered oxide is varied depending on the contents of the alkali metal element and silicon and/or the aluminum metal element, but is usually 800 to 1,500° C., preferably 900 to 1,300° C. When the sintering temperature is lower than 800° C., it is difficult to obtain a sufficiently inert sintered oxide, and when it is higher than 1,500° C., the time needed for the sintering step may become longer, and moreover, the step may cost a great deal.

As a further preferred process of preparing the sintered oxide, there can be mentioned a process comprising adding a compound containing an alkali metal element to an oxide comprising an alkali metal element and silica and/or alumina and sintered at 800 to 1,500° C., followed by calcining the mixture at 400 to 1,000° C. According to this process, unnecessary acid sites disappear completely to give a completely inert sintered oxide. As a process for addition of the compound containing an alkali metal element, every known process can be applied. However, preferred is a process comprising impregnating the above sintered oxide comprising an alkali metal element and silica and/or alumina with an aqueous solution of a hydroxide, carbonate or nitrate, particularly preferably hydroxide of an alkali metal element. The concentration of the aqueous solution of an alkali metal element can appropriately be selected, but in the case of the hydroxide, it is 0.1 to 5.0% by weight.

The shape of the sintered oxide used in the invention is varied depending on models and operation conditions of the heater (gas preheater), the reactor and the cooler, but usually, it is spherical or columnar. The size of the sintered oxide is usually in the range of 0.1 to 20 mm, and preferably in the range of 2 to 10 mm.

① In the case of a heat exchanger type reactor using a heat medium such as an oil or a molten salt, the sintered oxide comprising an alkali metal element and silica and/or alumina of the invention is loaded into the inlet side of the catalyst layer inside the reactor (for example, it is spread on the surface on the catalyst layer).

② In the case of an adiabatic reactor, the sintered oxide of the invention is loaded inside the heater (gas preheater) connected to the reactor through piping. By thus loading the sintered oxide, the raw material gas is heated to a predetermined temperature without being deteriorated. The sintered oxide, as a loading material, spread on the surface of the catalyst layer also has an effect of preventing the catalyst from moving with the raw material gas and putting the flow of the raw material gas in order.

③ The sintered oxide of the invention can also be used as a supporting material for fixation of the position of the catalyst. For example, when it is loaded as a catalyst-supporting layer into the outlet side of the catalyst layer inside the reactor, it is effective not only for supporting the catalyst, but also for preventing the raw material gas and the reaction gas from being retained and deteriorated.

④ The sintered oxide can further also be used as a loading material in the cooler for immediately cooling the reaction gas of high temperature which came out of the catalyst layer of one of various reactors.

⑤ Since the sintered oxide is inert to the solid oxide catalyst containing an alkali metal element, it can also be used as a diluent of the catalyst. For example, when reaction heat is large or when carbides, etc. adhering on the catalyst by the reaction are burned, local temperature change due to generation or absorption of heat can be inhibited by using a mixture of the catalyst with the sintered oxide.

The reaction temperature in use of the sintered oxide is usually 200 to 600° C., preferably 300 to 500° C.

In the process of the invention, a reactor of any model among fixed bed type, moving bed type and fluidized bed type can be used, but preferred is a fixed bed type reactor. As a heat transfer method of the reactor, any method can be applied, and ① a multi-tubular heat exchange method using a heat medium (molten salt, etc.) or ② an adiabatic method wherein there is no heat exchange with the surroundings is particularly preferred.

The reaction pressure in the invention is, usually, ordinary pressure or reduced pressure, but applied pressure is also possible. The reaction temperature is varied depending on the kind of reaction raw materials and other reaction conditions, but is 200 to 600° C., preferably 300 to 500° C.

EXAMPLES

The invention is specifically described below by examples, but the invention should not be limited thereby at all. The decomposition ratio, the conversion, the selectivity and the one-pass yield in the examples are supposed to obey the following definitions.

Decomposition ratio (% by mole)=(mole number of consumed compound/mole number of fed compound)×100

Conversion (% by mole)=(mole number of consumed glycol ether/mole number of fed glycol ether)×100

Selectivity (% by mole)=(mole number of formed unsaturated ether/mole number of consumed glycol ether)×100

One-pass yield (% by mole)=(mole number of formed unsaturated ether/mole number of fed glycol ether)×100

The acid-base strength of a sintered oxide was detected by the following method: 0.05 g of a sintered oxide dried at 180° C. for 2 hours is put in a test tube containing about 5 ml of anhydrous benzene, about 0.1 ml of a Hammett indicator solution (Methyl Red: pKa=4.8) is added, and presence or absence of formation of the acidity color is observed.

Example 1

Water (100 g) was added to 200 g of montmorillonite ($SiO_2$: 58.0%, $Al_2O_3$: 21.9%, $Na_2O$: 3.0%, $Fe_2O_3$: 1.9%, MgO: 3.4%, CaO: 0.5%) as a clay mineral, and the mixture was kneaded and molded into columns (diameter 5 mm and length 5 mm).

The columns were dried in the air at 120° C. for 20 hours, and sintered in the air at 1,400° C. for 2 hours to obtain a sintered oxide.

This sintered oxide (20 cc) was loaded into a stainless steel reaction tube having an inside diameter of 10 mm, the reaction tube was immersed in molten salt of 400° C., liquid 2-ethoxyethanol and nitrogen were fed into the reaction tube at velocities of 4.5 g/hr and 3,000 cc/hr, respectively to carry out decomposition reaction. When the reaction gas at one hour after the start of the feed was analyzed by gas chromatography, the decomposition ratio of 2-ethoxyethanol was 0.4% by mole. Since this sintered oxide was colored, the presence or absence of coloring by Hammett indicator could not be judged.

Example 2

Silicon oxide ($SiO_2$: 99.7%, $Na_2O$: <0.1%) (200 g) was added into a solution of 13.5 g of cesium carbonate in 450 g of water, and the mixture was kneaded and molded into columns (diameter 5 mm and length 7 mm).

The columns were dried in the air at 120° C. for 20 hours, and sintered in the air at 1,000° C. for 2 hours to obtain a sintered oxide.

This sintered oxide (20 cc) was loaded into a stainless steel reaction tube having an inside diameter of 10 mm, the reaction tube was immersed in molten salt of 400° C., liquid 2-ethoxyethanol and nitrogen were fed into the reaction tube at velocities of 4.5 g/hr and 3,000 cc/hr, respectively to carry out decomposition reaction. When the reaction gas at one hour after the start of the feed was analyzed by gas chromatography, the decomposition ratio of 2-ethoxyethanol was 0.3% by mole. Discoloration by Hammett indicator was not observed on this sintered oxide.

Comparative Example 1

Water (450 g) was added to 200 g of silicon oxide ($SiO_2$: 99.7%, $Al_2O_3$: <0.1%, $Na_2O$: <0.1%), and the mixture was kneaded and molded into columns (diameter 5 mm and length 7 mm). The columns were dried in the air at 120° C. for 20 hours, and sintered in the air at 1,000° C. for 2 hours to obtain a sintered oxide. Decomposition reaction was carried out in the same manner as in Example 2 using this sintered oxide. When the reaction gas at one hour after the start of the feed was analyzed by gas chromatography, the decomposition ratio of 2-ethoxyethanol was 3.3% by mole. Discoloration to the acidity color by Hammett indicator was observed on this sintered oxide.

Comparative Example 2

Zirconium oxide ($ZrO_2$: >99%) (200 g) was added into a solution of 4.0 g of sodium hydroxide in 200 g of water, and the mixture was concentrated to dryness while kneaded on a water bath and molded into columns (diameter 5 mm and length 5 mm).

The columns were sintered in the air at 1,000° C. for 2 hours to obtain a sintered oxide. Decomposition reaction was carried out in the same manner as in Example 2 using this sintered oxide. When the reaction gas at one hour after the start of the feed was analyzed by gas chromatography, the decomposition ratio of 2-ethoxyethanol was 9.2% by mole.

Example 3

Montmorillonite type silica ($SiO_2$: 73.4%, $Al_2O_3$: 14.0%, $Na_2O$: <0.1%) as a clay mineral (200 g) was added into a solution of 4.0 g of sodium hydroxide in 200 g of water, and the mixture was kneaded and molded into columns (diameter 5 mm and length 5 mm). The columns were dried in the air at 120° C. for 20 hours, and sintered in the air at 1,200° C. for 2 hours to obtain a sintered oxide.

This sintered oxide (20 cc) was loaded into a stainless steel reaction tube having an inside diameter of 10 mm, the reaction tube was immersed in molten salt of 370° C., liquid 2-ethoxyethanol and nitrogen were fed into the reaction tube at velocities of 4.5 g/hr and 3,000 cc/hr, respectively to carry out decomposition reaction. When the reaction gas at one hour after the start of the feed was analyzed by gas chromatography, the decomposition ratio of 2-ethoxyethanol was 0.3% by mole. Since this sintered oxide was colored, the presence or absence of coloring by Hammett indicator could not be judged.

Comparative Example 3

Water (200 g) was added to 200 g of montmorillonite type silicon oxide ($SiO_2$: 73.4%, $Al_2O_3$: 14.0%, $Na_2O$: <0.1%) as a clay mineral (200 g), and the mixture was kneaded and molded into columns (diameter 5 mm and length 7 mm). The columns were dried in the air at 120° C. for 20 hours, and sintered in the air at 1,200° C. for 2 hours to obtain a sintered oxide. Decomposition reaction was carried out in the same manner as in Example 3 using this sintered oxide. When the reaction gas at one hour after the start of the feed was analyzed by gas chromatography, the decomposition ratio of 2-ethoxy-ethanol was 3.8% by mole. Since this sintered oxide was colored, the presence or absence of coloring by Hammett indicator could not be judged.

Example 4

Decomposition reaction was carried out in the same manner as in Example 3 except that N-(2-hydroxyethyl)-2-pyrrolidone was used in place of 2-ethoxyethanol. When the reaction gas at one hour after the start of the feed was analyzed by gas chromatography, the decomposition ratio of N-(2-hydroxyethyl)-2-pyrrolidone was 0.1% by mole.

Example 5

Decomposition reaction was carried out in the same manner as in Example 3 except that monoethanolamine was used in place of 2-ethoxyethanol. When the reaction gas at one hour after the start of the feed was analyzed by gas chromatography, the decomposition ratio of monoethanolamine was 0.1% by mole.

Example 6

Decomposition reaction was carried out in the same manner as in Example 3 except that isobutyl vinyl ether was used in place of 2-ethoxyethanol. When the reaction gas at one hour after the start of the feed was analyzed by gas chromatography, the decomposition ratio of isobutyl vinyl ether was 0.2% by mole.

Example 7

Decomposition reaction was carried out in the same manner as in Example 3 except that a mixed liquid of p-cresol and methanol (mole ratio 1:3) was used in place of 2-ethoxyethanol, and the reaction tube was immersed in molten salt of 350° C. When the reaction gas at one hour after the start of the feed was analyzed by gas chromatography, the decomposition ratios of p-cresol and methanol were less than 0.1% by mole, respectively.

Example 8

A commercially available sintered oxide of spherical silica-alumina ($SiO_2$: 71.2%, $Al_2O_3$: 20.5%, $K_2O$: 4.9%, $Na_2O$: 1.8%, $TiO_2$: 0.2%, $Fe_2O_3$: 0.6%; diameter: 4 mm; apparent porosity: 0.1%; water absorption ratio: 0.1%) (20 cc) was loaded into a stainless steel reaction tube having an inside diameter of 10 mm, the reaction tube was immersed in molten salt of 460° C., liquid 2-ethoxyethanol and nitrogen were fed into the reaction tube at velocities of 4.5 g/hr and 3,000 cc/hr, respectively to carry out decomposition reaction. When the reaction gas at two hour after the start of the feed was analyzed by gas chromatography, the decomposition ratio of 2-ethoxyethanol was 0.9% by mole. Discoloration by Hammett indicator was not observed on this sintered oxide.

Example 9

A commercially available sintered oxide of spherical α-alumina ($SiO_2$: 12.0%, $Al_2O_3$: 86.1%, $K_2O$: 0.4%, $Na_2O$: 0.2%, CaO: 0.6%, MgO: 0.4%, $TiO_2$: 0.2%; diameter: 3 mm; specific surface area: <0.1 $m^2/g$) (20 cc) was loaded into a stainless steel reaction tube having an inside diameter of 10 mm, the reaction tube was immersed in molten salt of 400° C., liquid 2-ethoxyethanol and nitrogen were fed into the reaction tube at velocities of 4.5 g/hr and 3,000 cc/hr, respectively to carry out decomposition reaction. When the reaction gas at two hour after the start of the feed was analyzed by gas chromatography, the decomposition ratio of 2-ethoxyethanol was 0.4% by mole. Discoloration by Hammett indicator was not observed on this sintered oxide.

Comparative Example 4

Decomposition reaction was carried out in the same manner as in Example 8 except that commercially available spherical α-alumina ($Al_2O_3$: >99.6%; diameter: 3 mm; specific surface area: <1 $m^2/g$) was used. When the reaction gas at one hour after the start of the feed was analyzed by gas chromatography, the decomposition ratio of 2-ethoxyethanol was 8.4% by mole.

Example 10

Commercially available borosilicate glass (20 cc) was loaded into a stainless steel reaction tube having an inside diameter of 10 mm, the reaction tube was immersed in molten salt of 350° C., liquid N-vinyl-2-pyrrolidone and nitrogen were fed into the reaction tube at velocities of 4.5 g/hr and 3,000 cc/hr, respectively to carry out decomposition reaction. When the reaction gas at one hour after the start of the feed was analyzed by gas chromatography, the decomposition ratio of N-vinyl-2-pyrrolidone was 0.1% by mole. Discoloration to the acidity color by Hammett indicator was not observed on this sintered oxide.

Example 11

A commercially available sintered oxide of spherical silica-alumina ($SiO_2$: 71.2%, $Al_2O_3$: 20.5%, $K_2O$: 4.9%, $Na_2O$: 1.8%, $TiO_2$: 0.2%, $Fe_2O_3$: 0.6%; diameter: 4 mm; apparent porosity: 0.1%; water absorption ratio: 0.1%) (200 cc) was immersed in 100 cc of an aqueous 1.0% by weight sodium hydroxide solution for 2 hours, dried at 120° C. for 2 hours, and calcined in the air at 800° C. for 2 hours, to obtain a sintered oxide.

This sintered oxide (20 cc) was loaded into a stainless steel reaction tube having an inside diameter of 10 mm, the reaction tube was immersed in molten salt of 460° C., liquid 2-ethoxyethanol and nitrogen were fed into the reaction tube at velocities of 4.5 g/hr and 3,000 cc/hr, respectively to carry out decomposition reaction. When the reaction gas at one hour after the start of the feed was analyzed by gas chromatography, the decomposition ratio of 2-ethoxyethanol was 0.2% by mole. Discoloration to the acidity color by Hammett indicator was not observed on this sintered oxide.

Example 12

Silicon oxide (300 g) was added into a solution of 25 g of cesium hydroxide in 1,000 g of water, and the mixture was concentrated while kneaded on a water bath and molded into columns (diameter 5 mm and length 7 mm). The columns were dried in the air at 120° C. for 8 hour and calcined in the air at 500° C. for 2 hours to obtain a catalyst having a composition of $Cs_1Si_{30}$ as the composition ratio excluding oxygen.

A catalyst layer consisting of 1,000 cc of this catalyst, a catalyst-supporting layer consisting of 500 cc of the sintered oxide of Example 11 which is located at the outlet of the catalyst layer, and a raw material gas-preheating layer consisting of 1,000 cc of the sintered oxide of Example 11 which is located at the inlet side of the catalyst layer were loaded into a reaction tube having an inside diameter of 30 mm.

Then, the inside temperature of the reaction tube was raised to 370° C., and the temperature was maintained while the inside of the reaction tube was made to have a reduced pressure. While the outlet pressure of the reaction tube was maintained at $30.7 \times 10^3$ Pa (230 mmHg), 2-ethoxyethanol was continuously fed at a velocity of 402 g/hr (space velocity as gas of 100 $h^{-1}$). When the reaction gas at 24 hours after the start of the feed was analyzed by gas chromatography, the conversion ratio of 2-ethoxyethanol was 22.4% by mole, the selectivity of ethyl vinyl ether was 93.0% by mole, and the one-pass yield was 20.8% by mole.

EFFECT OF THE INVENTION

The process of the invention displays such an improvement effect that in a gas-phase dehydration reaction using a solid oxide catalyst containing an alkali metal element, preheating of the raw material gas and/or support of the catalyst can efficiently be carried out, and moreover, deterioration of the raw material gas and the objective product can be inhibited. Thus, by the invention, an industrially advantageous gas-phase dehydration reaction process is provided.

What is claimed is:

1. A process of gas-phase dehydration reaction comprising contacting a raw material gas with a solid oxide catalyst containing an alkali metal element, wherein a sintered oxide comprising an alkali metal element and silica and/or alumina is used as a loading material for preheating of the raw material gas and/or as a supporting material for fixation of the position of the catalyst.

2. The process of gas-phase dehydration reaction according to claim 1 wherein the solid oxide catalyst is a solid oxide containing an alkali metal element and silicon.

3. The process of gas-phase dehydration reaction according to claim 1 wherein the sintered oxide is a sintered oxide obtained by adding a compound containing an alkali metal element to a sintered oxide comprising an alkali metal element and silica and/or alumina, followed by calcining the mixture.

4. The process of gas-phase dehydration reaction according to claim 2 wherein the sintered oxide is a sintered oxide obtained by adding a compound containing an alkali metal element to a sintered oxide comprising an alkali metal element and silica and/or alumina, followed by calcining the mixture.

5. The process of gas-phase dehydration reaction according to claim 1 wherein the raw material of the gas-phase dehydration reaction is a hydroxyethyl compound represented by the following general formula (I)

$$Z_1-CH(R_1)-CH(R_2)-OH \quad (I)$$

wherein $Z_1$ is an amino group, a monoalkylamino group having 1 to 6 carbon atoms, a mercapto group, an alkoxy group having 1 to 10 carbon atoms, an alkylcarboxylic acid amido group wherein the alkylcarboxylic acid moiety has 1 to 6 carbon atoms and the group binding to the N atom of the amido moiety is a hydrogen atom or a methyl group, or a cyclic carboxylic acid amido group including an alkylene group having 3 to 5 carbon atoms and $R_1$ and $R_2$ are each, independently, a hydrogen atom, a methyl group or an ethyl group.

6. The process of gas-phase dehydration reaction according to claim 2 wherein the raw material of the gas-phase dehydration reaction is a hydroxyethyl compound represented by the following general formula (I)

$$Z_1-CH(R_1)-CH(R_2)-OH \quad (I)$$

wherein $Z_1$ is an amino group, a monoalkylamino group having 1 to 6 carbon atoms, a mercapto group, an alkoxy group having 1 to 10 carbon atoms, an alkylcarboxylic acid amido group wherein the alkylcarboxylic acid moiety has 1 to 6 carbon atoms and the group binding to the N atom of the amido moiety is a hydrogen atom or a methyl group, or a cyclic carboxylic acid amido group including an alkylene group having 3 to 5 carbon atoms and $R_1$ and $R_2$ are each, independently, a hydrogen atom, a methyl group or an ethyl group.

7. The process of gas-phase dehydration reaction according to claim 3 wherein the raw material of the gas-phase dehydration reaction is a hydroxyethyl compound represented by the following general formula (I)

$$Z_1-CH(R_1)-CH(R_2)-OH \quad (I)$$

wherein $Z_1$ is an amino group, a monoalkylamino group having 1 to 6 carbon atoms, a mercapto group, an alkoxy group having 1 to 10 carbon atoms, an alkylcarboxylic acid amido group wherein the alkylcarboxylic acid moiety has 1 to 6 carbon atoms and the group binding to the N atom of the amido moiety is a hydrogen atom or a methyl group, or a cyclic carboxylic acid amido group including an alkylene group having 3 to 5 carbon atoms and $R_1$ and $R_2$ are each, independently, a hydrogen atom, a methyl group or an ethyl group.

8. The process of gas-phase dehydration reaction according to claim 4 wherein the raw material of the gas-phase dehydration reaction is a hydroxyethyl compound represented by the following general formula (I)

$$Z_1-CH(R_1)-CH(R_2)-OH \quad (I)$$

wherein $Z_1$ is an amino group, a monoalkylamino group having 1 to 6 carbon atoms, a mercapto group, an alkoxy group having 1 to 10 carbon atoms, an alkylcarboxylic acid amido group wherein the alkylcarboxylic acid moiety has 1 to 6 carbon atoms and the group binding to the N atom of the amido moiety is a hydrogen atom or a methyl group, or a cyclic carboxylic acid amido group including an alkylene group having 3 to 5 carbon atoms and $R_1$ and $R_2$ are each, independently, a hydrogen atom, a methyl group or an ethyl group.

9. The process of gas-phase dehydration reaction according to claim 1 wherein the gas-phase dehydration reaction is a reaction comprising gas-phase intermolecular dehydration of a hydroxyethyl compound represented by the following general formula (II)

$$Z_2\text{—}CH_2\text{—}CH_2\text{—}OH \qquad (II)$$

to convert it to a vinyl compound represented by the following general formula (III)

$$Z_2\text{—}CH\text{=}CH_2 \qquad (III)$$

wherein $Z_2$ is an alkoxy group having 1 to 10 carbon atoms, an alkylcarboxylic acid amido group wherein the alkylcarboxylic acid moiety has 1 to 6 carbon atoms and the group binding to the N atom of the amido moiety is a hydrogen atom or a methyl group, or a cyclic carboxylic acid amido group including an alkylene group having 3 to 5 carbon atoms.

10. The process of gas-phase dehydration reaction according to claim 2 wherein the gas-phase dehydration reaction is a reaction comprising gas-phase intermolecular dehydration of a hydroxyethyl compound represented by the following general formula (II)

$$Z_2\text{—}CH_2\text{—}CH_2\text{—}OH \qquad (II)$$

to convert it to a vinyl compound represented by the following general formula (III)

$$Z_2\text{—}CH\text{=}CH_2 \qquad (III)$$

wherein $Z_2$ is an alkoxy group having 1 to 10 carbon atoms, an alkylcarboxylic acid amido group wherein the alkylcarboxylic acid moiety has 1 to 6 carbon atoms and the group binding to the N atom of the amido moiety is a hydrogen atom or a methyl group, or a cyclic carboxylic acid amido group including an alkylene group having 3 to 5 carbon atoms.

11. The process of gas-phase dehydration reaction according to claim 3 wherein the gas-phase dehydration reaction is a reaction comprising gas-phase intermolecular dehydration of a hydroxyethyl compound represented by the following general formula (II)

$$Z_2\text{—}CH_2\text{—}CH_2\text{—}OH \qquad (II)$$

to convert it to a vinyl compound represented by the following general formula (III)

$$Z_2\text{—}CH\text{=}CH_2 \qquad (III)$$

wherein $Z_2$ is an alkoxy group having 1 to 10 carbon atoms, an alkylcarboxylic acid amido group wherein the alkylcarboxylic acid moiety has 1 to 6 carbon atoms and the group binding to the N atom of the amido moiety is a hydrogen atom or a methyl group, or a cyclic carboxylic acid amido group including an alkylene group having 3 to 5 carbon atoms.

12. The process of gas-phase dehydration reaction according to claim 4 wherein the gas-phase dehydration reaction is a reaction comprising gas-phase intermolecular dehydration of a hydroxyethyl compound represented by the following general formula (II)

$$Z_2\text{—}CH_2\text{—}CH_2\text{—}OH \qquad (II)$$

to convert it to a vinyl compound represented by the following general formula (III)

$$Z_2\text{—}CH\text{=}CH_2 \qquad (III)$$

wherein $Z_2$ is an alkoxy group having 1 to 10 carbon atoms, an alkylcarboxylic acid amido group wherein the alkylcarboxylic acid moiety has 1 to 6 carbon atoms and the group binding to the N atom of the amido moiety is a hydrogen atom or a methyl group, or a cyclic carboxylic acid amido group including an alkylene group having 3 to 5 carbon atoms.

13. The process of gas-phase dehydration reaction according to claim 5 wherein the gas-phase dehydration reaction is a reaction comprising gas-phase intermolecular dehydration of a hydroxyethyl compound represented by the following general formula (II)

$$Z_2\text{—}CH_2\text{—}CH_2\text{—}OH \qquad (II)$$

to convert it to a vinyl compound represented by the following general formula (III)

$$Z_2\text{—}CH\text{=}CH_2 \qquad (III)$$

wherein $Z_2$ is an alkoxy group having 1 to 10 carbon atoms, an alkylcarboxylic acid amido group wherein the alkylcarboxylic acid moiety has 1 to 6 carbon atoms and the group binding to the N atom of the amido moiety is a hydrogen atom or a methyl group, or a cyclic carboxylic acid amido group including an alkylene group having 3 to 5 carbon atoms.

14. The process of gas-phase dehydration reaction according to claim 6 wherein the gas-phase dehydration reaction is a reaction comprising gas-phase intermolecular dehydration of a hydroxyethyl compound represented by the following general formula (II)

$$Z_2\text{—}CH_2\text{—}CH_2\text{—}OH \qquad (II)$$

to convert it to a vinyl compound represented by the following general formula (III)

$$Z_2\text{—}CH\text{=}CH_2 \qquad (III)$$

wherein $Z_2$ is an alkoxy group having 1 to 10 carbon atoms, an alkylcarboxylic acid amido group wherein the alkylcarboxylic acid moiety has 1 to 6 carbon atoms and the group binding to the N atom of the amido moiety is a hydrogen atom or a methyl group, or a cyclic carboxylic acid amido group including an alkylene group having 3 to 5 carbon atoms.

15. The process of gas-phase dehydration reaction according to claim 7 wherein the gas-phase dehydration reaction is a reaction comprising gas-phase intermolecular dehydration of a hydroxyethyl compound represented by the following general formula (II)

$$Z_2\text{—}CH_2\text{—}CH_2\text{—}OH \qquad (II)$$

to convert it to a vinyl compound represented by the following general formula (III)

$$Z_2-CH=CH_2 \quad (III)$$

wherein $Z_2$ is an alkoxy group having 1 to 10 carbon atoms, an alkylcarboxylic acid amido group wherein the alkylcarboxylic acid moiety has 1 to 6 carbon atoms and the group binding to the N atom of the amido moiety is a hydrogen atom or a methyl group, or a cyclic carboxylic acid amido group including an alkylene group having 3 to 5 carbon atoms.

16. The process of gas-phase dehydration reaction according to claim 8 wherein the gas-phase dehydration reaction is a reaction comprising gas-phase intermolecular dehydration of a hydroxyethyl compound represented by the following general formula (II)

$$Z_2-CH_2-CH_2-OH \quad (II)$$

to convert it to a vinyl compound represented by the following general formula (III)

$$Z_2-CH=CH_2 \quad (III)$$

wherein $Z_2$ is an alkoxy group having 1 to 10 carbon atoms, an alkylcarboxylic acid amido group wherein the alkylcarboxylic acid moiety has 1 to 6 carbon atoms and the group binding to the N atom of the amido moiety is a hydrogen atom or a methyl group, or a cyclic carboxylic acid amido group including an alkylene group having 3 to 5 carbon atoms.

17. The process of gas-phase dehydration reaction according to claim 1 wherein the gas-phase dehydration reaction is a reaction comprising gas-phase intermolecular dehydration of a hydroxyethyl compound represented by the following general formula (IV)

$$R_3-NH-CH_2-CH_2-OH \quad (IV)$$

to convert it to a cyclic amine represented by the general formula (V)

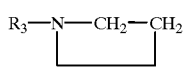
(V)

wherein $R_3$ is a hydrogen atom or an alkyl group having 1 to 6 carbon atoms.

18. The process of gas-phase dehydration reaction according to claim 2 wherein the gas-phase dehydration reaction is a reaction comprising gas-phase intermolecular dehydration of a hydroxyethyl compound represented by the following general formula (IV)

$$R_3-NH-CH_2-CH_2-OH \quad (IV)$$

to convert it to a cyclic amine represented by the general formula (V)

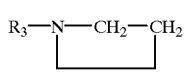
(V)

wherein $R_3$ is a hydrogen atom or an alkyl group having 1 to 6 carbon atoms.

19. The process of gas-phase dehydration reaction according to claim 3 wherein the gas-phase dehydration reaction is a reaction comprising gas-phase intermolecular dehydration of a hydroxyethyl compound represented by the following general formula (IV)

$$R_3-NH-CH_2-CH_2-OH \quad (IV)$$

to convert it to a cyclic amine represented by the general formula (V)

(V)

wherein $R_3$ is a hydrogen atom or an alkyl group having 1 to 6 carbon atoms.

20. The process of gas-phase dehydration reaction according to claim 4 wherein the gas-phase dehydration reaction is a reaction comprising gas-phase intermolecular dehydration of a hydroxyethyl compound represented by the following general formula (IV)

$$R_3-NH-CH_2-CH_2-OH \quad (IV)$$

to convert it to a cyclic amine represented by the general formula (V)

(V)

wherein $R_3$ is a hydrogen atom or an alkyl group having 1 to 6 carbon atoms.

21. The process of gas-phase dehydration reaction according to claim 5 wherein the gas-phase dehydration reaction is a reaction comprising gas-phase intermolecular dehydration of a hydroxyethyl compound represented by the following general formula (IV)

$$R_3-NH-CH_2-CH_2-OH \quad (IV)$$

to convert it to a cyclic amine represented by the general formula (V)

(V)

wherein $R_3$ is a hydrogen atom or an alkyl group having 1 to 6 carbon atoms.

22. The process of gas-phase dehydration reaction according to claim 6 wherein the gas-phase dehydration reaction is a reaction comprising gas-phase intermolecular dehydration of a hydroxyethyl compound represented by the following general formula (IV)

$$R_3-NH-CH_2-CH_2-OH \quad (IV)$$

to convert it to a cyclic amine represented by the general formula (V)

(V)

wherein $R_3$ is a hydrogen atom or an alkyl group having 1 to 6 carbon atoms.

23. The process of gas-phase dehydration reaction according to claim 7 wherein the gas-phase dehydration reaction is a reaction comprising gas-phase intermolecular dehydration of a hydroxyethyl compound represented by the following general formula (IV)

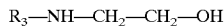  (IV)

to convert it to a cyclic amine represented by the general formula (V)

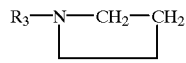  (V)

wherein $R_3$ is a hydrogen atom or an alkyl group having 1 to 6 carbon atoms.

24. The process of gas-phase dehydration reaction according to claim 8 wherein the gas-phase dehydration reaction is a reaction comprising gas-phase intermolecular dehydration of a hydroxyethyl compound represented by the following general formula (IV)

  (IV)

to convert it to a cyclic amine represented by the general formula (V)

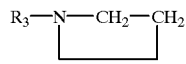  (V)

wherein $R_3$ is a hydrogen atom or an alkyl group having 1 to 6 carbon atoms.

25. The process of gas-phase dehydration reaction according to claim 9 wherein the gas-phase dehydration reaction is a reaction comprising gas-phase intermolecular dehydration of a hydroxyethyl compound represented by the following general formula (IV)

  (IV)

to convert it to a cyclic amine represented by the general formula (V)

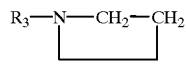  (V)

wherein $R_3$ is a hydrogen atom or an alkyl group having 1 to 6 carbon atoms.

26. The process of gas-phase dehydration reaction according to claim 10 wherein the gas-phase dehydration reaction is a reaction comprising gas-phase intermolecular dehydration of a hydroxyethyl compound represented by the following general formula (IV)

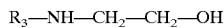  (IV)

to convert it to a cyclic amine represented by the general formula (V)

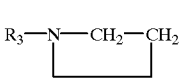  (V)

wherein $R_3$ is a hydrogen atom or an alkyl group having 1 to 6 carbon atoms.

27. The process of gas-phase dehydration reaction according to claim 11 wherein the gas-phase dehydration reaction is a reaction comprising gas-phase intermolecular dehydration of a hydroxyethyl compound represented by the following general formula (IV)

  (IV)

to convert it to a cyclic amine represented by the general formula (V)

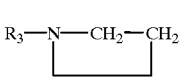  (V)

wherein $R_3$ is a hydrogen atom or an alkyl group having 1 to 6 carbon atoms.

28. The process of gas-phase dehydration reaction according to claim 12 wherein the gas-phase dehydration reaction is a reaction comprising gas-phase intermolecular dehydration of a hydroxyethyl compound represented by the following general formula (IV)

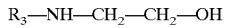  (IV)

to convert it to a cyclic amine represented by the general formula (V)

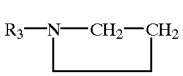  (V)

wherein $R_3$ is a hydrogen atom or an alkyl group having 1 to 6 carbon atoms.

29. The process of gas-phase dehydration reaction according to claim 13 wherein the gas-phase dehydration reaction is a reaction comprising gas-phase intermolecular dehydration of a hydroxyethyl compound represented by the following general formula (IV)

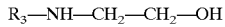  (IV)

to convert it to a cyclic amine represented by the general formula (V)

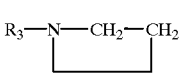  (V)

wherein $R_3$ is a hydrogen atom or an alkyl group having 1 to 6 carbon atoms.

30. The process of gas-phase dehydration reaction according to claim 14 wherein the gas-phase dehydration reaction is a reaction comprising gas-phase intermolecular dehydra tion of a hydroxyethyl compound represented by the following general formula (IV)

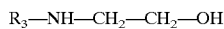    (IV)

to convert it to a cyclic amine represented by the general formula (V)

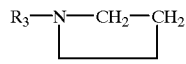    (V)

wherein $R_3$ is a hydrogen atom or an alkyl group having 1 to 6 carbon atoms.

31. The process of gas-phase dehydration reaction according to claim 15 wherein the gas-phase dehydration reaction is a reaction comprising gas-phase intermolecular dehydration of a hydroxyethyl compound represented by the following general formula (IV)

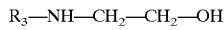    (IV)

to convert it to a cyclic amine represented by the general formula (V)

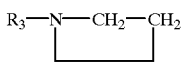    (V)

wherein $R_3$ is a hydrogen atom or an alkyl group having 1 to 6 carbon atoms.

32. The process of gas-phase dehydration reaction according to claim 16 wherein the gas-phase dehydration reaction is a reaction comprising gas-phase intermolecular dehydration of a hydroxyethyl compound represented by the following general formula (IV)

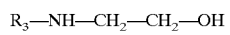    (IV)

to convert it to a cyclic amine represented by the general formula (V)

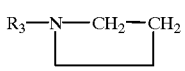    (V)

wherein $R_3$ is a hydrogen atom or an alkyl group having 1 to 6 carbon atoms.

* * * * *